US007883648B2

(12) United States Patent
Kazakov et al.

(10) Patent No.: US 7,883,648 B2
(45) Date of Patent: *Feb. 8, 2011

(54) LIPOBEADS AND THEIR PRODUCTION

(75) Inventors: Sergey Kazakov, White Plains, NY (US); Marian Kaholek, Bloomfield, NJ (US); Kalle Levon, New York, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/619,090

(22) Filed: Nov. 16, 2009

(65) Prior Publication Data
US 2010/0062054 A1  Mar. 11, 2010

Related U.S. Application Data

(62) Division of application No. 10/218,553, filed on Aug. 14, 2002, now Pat. No. 7,618,565.

(60) Provisional application No. 60/312,878, filed on Aug. 16, 2001.

(51) Int. Cl.
C08J 3/28 (2006.01)
C08F 2/50 (2006.01)
B01J 13/02 (2006.01)
B01J 13/14 (2006.01)
B01J 13/20 (2006.01)

(52) U.S. Cl. .............................. 264/4.1; 264/4; 264/4.3; 264/4.33; 264/4.6; 264/4.7; 522/84; 522/86; 522/85; 522/104; 522/107; 522/113; 522/117; 522/116; 522/120; 522/121; 522/153; 522/150; 522/154; 522/178; 522/179; 522/182; 428/402; 428/402.2; 428/402.21; 428/402.22; 428/402.24; 428/403

(58) Field of Classification Search .................. 522/84, 522/86, 85, 104, 107, 113, 114, 117, 116, 522/120, 121, 150, 153, 154, 178, 179, 182, 522/183, 54; 526/200, 287, 306, 323.1; 264/4, 264/4.1, 4.3, 4.33, 4.7, 4.6; 428/402, 402.2, 428/402.21, 402.22, 402.24, 403
See application file for complete search history.

(56) References Cited

U.S. PATENT DOCUMENTS 7,618,565 B2 * 11/2009 Kazakov et al. .............. 264/4.1
2003/0044455 A1 * 3/2003 Kazakov et al. ............. 424/450

* cited by examiner

*Primary Examiner*—Sanza L McClendon
(74) *Attorney, Agent, or Firm*—Straub & Pokotylo; John C. Pokotylo

(57) ABSTRACT

Lipobeads (liposome-encapsulated hydrogels) combine properties of hydrogels and liposomes to create systems that are sensitive to environmental conditions and respond to changes in those conditions in a fast time scale. Lipobeads may be produced by polymerizing anchored or unanchored hydrogels within liposomes or by mixing anchored or unanchored hydrogels with liposomes. Giant lipobeads may be produced by shrinking unanchored nanogels in lipobeads and fusing the resulting lipobead aggregates, long-term aging of anchored or unanchored lipobeads, or mixing anchored or unanchored aggregated nanogels with liposomes. Poly(acrylamide), poly(N-isopropylacrylamide), and poly(N-isopropylacrylamide-co-1-vinylimidazole) lipobeads were produced and characterized.

24 Claims, 16 Drawing Sheets

Aggregate of lipobeads

Giant lipobead

Figure 13

Composition of hydrogel-forming media and properties of macroscopic hydrogels studied

| Hydrogel | [AAm] (wt%) | [NIPA] (wt%) | [VI] (wt%) | [MBA] (wt%) | [DEAP] (wt%) | Dilution (times) | $\tau_P$ (h) | Sensitivity | $\alpha$ |
|---|---|---|---|---|---|---|---|---|---|
| PAA | 4.73 | - | - | 0.47 | 0.10 | 20 | 2 | Acetone: 40 vol % | ~0.07 |
| PNIPA | - | 5.10 | - | 0.51 | 0.10 | 20 | 2 | $T_V$~32 °C | ~0.12 |
| PNIPA-VI | - | 5.51 | 1.97 | 0.50 | 0.10 | 25 | 2 | $T_V$~37 °C | ~0.14 |
| PNIPA-VI | - | 5.51 | 1.97 | 0.50 | 0.10 | 25 | 2 | pH | ~6 |

LIPOBEADS AND THEIR PRODUCTION

RELATED APPLICATIONS

This application is a divisional of U.S. patent application Ser. No. 10/218,553 (referred to as "the '553 application" and incorporated herein by references), titled "LIPOBEADS AND THEIR PRODUCTION," filed on Aug. 14, 2002, listing Sergey Kazakov, Marian Kaholek, and Kalle Levon as the inventors, scheduled to issue as U.S. Pat. No. 7,618,565 on Nov. 17, 2009, and claiming benefit, under 35 U.S.C. §119(e)(1), to the filing date of provisional patent application Ser. No. 60/312,878 (referred to as "the '878 provisional" and incorporated herein by reference), entitled "UV-INDUCED GELATION ON NANOMETER SCALE USING LIPOSOME REACTOR", filed on Aug. 16, 2001 and listing Sergey Kazakov, Marian Kaholek, and Kalle Levon as the inventors, for any inventions disclosed in the manner provided by 35 U.S.C. §112, ¶1.

FEDERALLY SPONSORED RESEARCH

This invention was made with Government support and the Government has certain rights in the invention as provided for by contract number 0660076225 awarded by DARPA.

BACKGROUND

1. Field of the Invention

The present invention concerns nanogels encapsulated within a lipid bilayer (lipobeads) and their production.

2. Related Art

Artificial systems consisting of only spherical hydrogel particles or liposomes have already found a variety of biomedical applications in drug delivery, drug targeting, protein separation, enzyme immobilization and so on. Sensory properties of the combined liposome-hydrogel structures may lead to novel biomimetic sensory systems.

Liposomes are phospholipid assemblies consisting of a flexible, cell membrane-like lipid bilayer, the surface of which acts as a permeability barrier. Different compounds can be entrapped in the liposome's aqueous interior. It has been shown that liposomes can be constructed with bilayer permeability responsive to a variety of physical and chemical stimuli, including temperature, light, pH, and ions (See, e.g., G. Gregoriadis et al., *Vesicles*, Marcel Dekker: New York (1996). This book is incorporated herein by reference.). These liposomes can mimic various functions of biological membranes and can be used as a container for storage, transport, and controllable release of compounds. Liposomes can be mechanically unstable, however and their loading capacity is limited by the water solubility of the material to be loaded.

Hydrogel particles are mechanically more stable than liposomes because of cross-linking and have larger loading capacities than liposomes. Their properties (swelling/deswelling) can be more sensitive to environmental conditions. It has been reported that some polymer gels can swell or shrink discontinuously and reversibly in response to many different stimuli (temperature, pH, ions, electric fields or light) depending on the chemical composition of the gel/solvent system. The volume change can be as large as a thousand-fold. Macroscopic gels respond to the environmental changes on a rather long-time scale, however. (See, e.g., the article Tanaka et al., *J. Chem. Phys.*, 90: 5161 (1989). This article is incorporated herein by reference.) The Tanaka article showed that for a spherical gel, the time required for swelling or shrinking is proportional to the square of its radius. Therefore, smaller hydrogels should swell/deswell faster. Such smaller hydrogels (e.g., having a diameter on a nanometer scale) should find more potential applications.

Nevertheless, hydrogels lack many useful surface properties of a lipid bilayer. Lipid bilayers stabilized on various supports (glass, plastic, metal, and modified polymer) (See, e.g., the articles: Bayer et al., *Biophys. J.*, 58: 357 (1990); Rothe et al., *FEBS. Lett.*, 263: 308 (1990); Plant, *Langmuir*, 9: 2764 (1993); Spinke et al., *Biophys. J.*, 63: 1667 (1992). These articles are incorporated herein by reference.) have found a number of applications (See, e.g., the articles: Sackman, *Science*, 271: 43 (1996); McConnell et al., *Biochim. Biophys. Acta*, 864: 95 (1986). These articles are incorporated herein by reference.). Bilayer membranes on solid supports are attractive systems mimicking the structural, sensing, and transport roles of biological membranes (See, e.g., the articles: Woodhouse et al., *Faraday Discuss*, 111: 247 (1998); Wagner et al., *Biophys. J.*, 79: 1400 (2000); Raguse et al., *Langmuir*, 14: 648 (1998); Cornell et al., *Nature*, 387: 580 (1997); Kasianowicz et al., *Anal. Chem.*, 73: 2268 (2001). These articles are incorporated herein by reference.), especially sensory systems using ion-channel switches (See, e.g., the articles Raguse et al., Cornell et al., and Kasianowicz et al.). The main drawback of the supported bilayer membranes to date is a lack of well-defined ionic reservoirs on both sides of the membrane.

A functional ionic reservoir between membrane and a substrate can be constructed using an ion sensitive hydrogel. In this context, combination of hydrogel particles with liposomes reconstituted with the membrane protein (ionic channel) can be considered as a model system to study the functions of membranes and membrane proteins and to design new sensory devices. An appropriate assembly of lipid bilayer on a spherical hydrogel surface can be used to prepare an artificial cell analogue. Furthermore, hydrogel-liposome assemblies combine the properties of both classes of materials, which broaden their potentials for biomimetic sensory systems, controlled release devices, and multivalent receptors.

Work on preparing and characterizing submicrometer-scale hydrogel particles has intensified recently, but there are few works devoted to fabricating different combinations of hydrogels and liposomes. A method of fabricating hydrogel spherical particles (beads) within liposomes was reported (See U.S. Pat. No. 5,626,870, hereafter referred to as "the Monshipouri patent"; V. P. Torchilin et al., *Macromol. Chem., Rapid Commun.* 8: 457 (1987), hereafter referred to as "the Torchilin article". These works are incorporated herein by reference.). Unfortunately, however, the method discussed in the Monshipouri patent required special hydrogel-forming substances with a gelation initiator for which a liposomal bilayer was permeable. The authors of the Torchilin article prepared LUV liposomes with average diameters of approximately 650 nm using the reverse phase evaporation method. This technique, however, makes it difficult to control liposome size and polydispersity, which is the reason that the Torchilin article presents only average sizes of the particles detected by dynamic light scattering. According to the Torchilin article, the detergent and phospholipid were not removed after solubilizing the lipid bilayer to release the hydrogel particles. Moreover, gels contained in liposomes and gel particles were not distinguished by scanning electron microscopy. Encapsulating hydrogel particles in liposomes was described (See, e.g., the article, Gao, K.; Huang L. *Biochim. Biophys. Acta*. 897: 377 (1987), hereafter referred to as "the Gao article". This article is incorporated herein by reference.). Although the overall mechanical strength of the liposomal structure discussed in the Gao article was enhanced in the latter system, the unanchored bilayer was still unstable and needed specific lipid mixtures and polymer cores of certain sizes and shapes. The article by Jin et al. (*FEBS Lett.* 397: 70 (1996). This article is incorporated herein by reference.) reported the design and preparation of a novel hydrogel-anchored lipid vesicle system, named "lipobeads". This system contained (i) a hydrogel polymer core anchored by fatty acids, which were covalently attached to the surface of the hydrogel and (ii) a lipid monolayer around the modified hydrogel spherical particle. In this system, the bilayer consisting of hydrophobic chains of fatty acids and hydrophobic tails of the phospholipids, was more stable than that in the system discussed in the Gao article. Spherical anionic microgels (6.5 μm at pH 7.0), composed of methylene-bis-acrylamide and methacrylic acid and loaded with doxorubicin, were coated with a lipid bilayer (See Kiser et al., *Nature*, 394: 459 (1998). This article is incorporated herein by reference.) to control swelling and release of doxorubicin from the microgels. (See, e.g., the article Yang et al., *J. Chromotogr. B.* 707: 131 (1998). This article is incorporated herein by reference.) Biotinylated small and large unilamellar liposomes were immobilized in avidin- or streptavidin-derived gel beads for chromatographic analysis. Recently, it was reported that egg phosphatidylcholine liposomes and biomembrane fragments could be immobilized on the surface of poly(acrylamide) macrogel containing hydrophobic anchors, which probably penetrated into the lipid bilayer (See, e.g., the article Yang, et al. *Mat. Sci. and Eng. C.* 13: 117 (2000)). In all of the above-referenced works (except the Monshipouri patent and the Torchilin article), the sizes of hydrogel particles varied on the micrometer scale. (In these works, optical or electron microscopy was used for characterization.) However, hydrogel particles with nanometer-range diameters would swell and shrink faster in response to environmental conditions because of their smaller radii.

In view of the limits of the state of the art, hydrogel/liposome systems that can respond to changes in the environment on a short time scale are needed.

SUMMARY OF THE INVENTION

The present invention describes preparing and characterizing hydrogel nanoparticles (nanogels) and liposomes. The present invention also describes different assemblies of nanogels and liposomes defining various hydrogel/liposome systems. These hydrogel/liposome systems will often combine complementary advantages of the liposomes and the polymeric hydrogels. Studying the individual behavior of the hydrogel particles and liposomes in aqueous solution affords better understanding of the behavior of the hydrogel/liposome system. The following systems were prepared and characterized: (i) an unanchored nanogel entrapped in a liposome; (ii) an anchored nanogel entrapped in a liposome; (iii) an aggregate of unanchored nanogels coated with phospholipid bilayer ("giant" lipobeads), (iv) an aggregate of anchored nanogels coated with phospholipid bilayer ("giant" lipobeads), (v) an aggregate of anchored and unanchored nanogels coated with phospholipid bilayer (combined giant lipobeads) and (vi) an aggregate of anchored lipobeads.

The present invention also describes the size distribution changes of the hydrogel particles, liposomes, and their assemblies in response to solvent variations, temperature variations, pH variations, and ionic strength variations.

BRIEF DESCRIPTION OF DRAWINGS

FIG. 13 is a table that lists the composition of hydrogel-forming media and properties of macroscopic hydrogels.

DETAILED DESCRIPTION

The present invention concerns lipobeads, giant lipobeads, their production, and their properties. The present invention functions to produce assemblies of liposome-encapsulated nanogel particles that respond to environmental conditions such as pH, temperature, and ions on a fast time scale. The following description is presented to one skilled in the art to make and use the invention, and is provided in the context of particular embodiments and methods. Various modifications to the disclosed embodiments and methods will be apparent to those skilled in the art, and the general principles set forth below may be applied to other embodiments, methods and applications. Thus, the present invention is not intended to be limited to the embodiments and methods shown and the inventors regard their invention as the following disclosed methods, apparatus and materials and any other patentable subject matter to the extent that they are patentable.

In the following, fabrication of nanogels, liposomes, lipobeads, and giant lipobeads is described in §4.1. Properties of the resulting liposomes, nanogels, lipobeads and giant lipobead systems are described in §4.2 in terms of exemplary embodiments.

Generating Hydrogel/Liposome Assemblies

In the following, generating liposomes and nanogels are described in §4.1.1 and §4.1.2. Combinations of hydrogels and liposomes, lipobeads and giant lipobeads, are described in §4.1.3 and §4.1.4.

Generating Liposomes

Liposome preparation is described in U.S. patent application Ser. No. 10/218,554, filed concurrently with the '553 application on Aug. 14, 2002, entitled NANOGELS AND THEIR PRODUCTION USING LIPOSOMES AS REACTORS, by Sergey Kazakov, Marian Kaholek, and Kalle Levon (This patent is incorporated herein by reference). Generally, this technique of preparing liposomes involves freezing and thawing a solution of multilamellar vesicles (MLV) followed by sonication to yield large unilamellar vesicles (LUV) within the range of average sizes from 30 to 1000 nm.

Generating Nanogels

Preparing hydrogels with nanometer-scale dimensions using liposomes as reactors was described in U.S. patent application Ser. No. 10/218,554, filed concurrently with the '553 application on Aug. 14, 2002, entitled NANOGELS AND THEIR PRODUCTION USING LIPOSOMES AS REACTORS, by Sergey Kazakov, Marian Kaholek, and Kalle Levon. In general, this technique of preparing nanogels involves (i) encapsulating hydrogel-forming components into the liposomes and (ii) polymerizing the encapsulated hydrogel-forming components.

Generating Lipobeads

The present invention may be used to produce lipobeads by (a) polymerizing hydrogel-forming components within liposomes, or (b) mixing nanogel particles with liposomes to form lipid bilayer-coated hydrogel particles.

Figure 1:
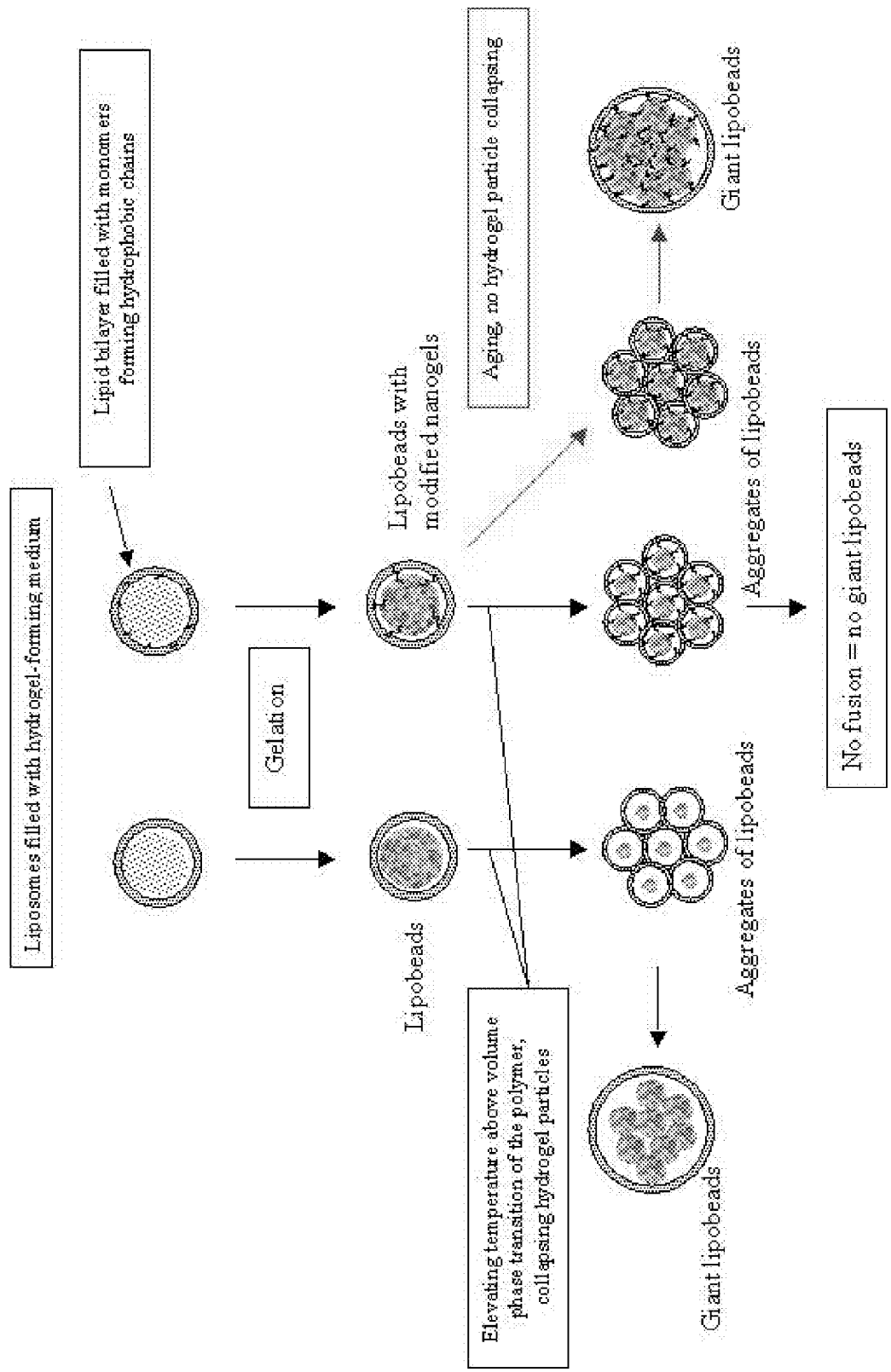
FIG. 1 is a scheme depicting lipobead preparation by polymerizing hydrogel-forming components within liposomes.
Figure 2:
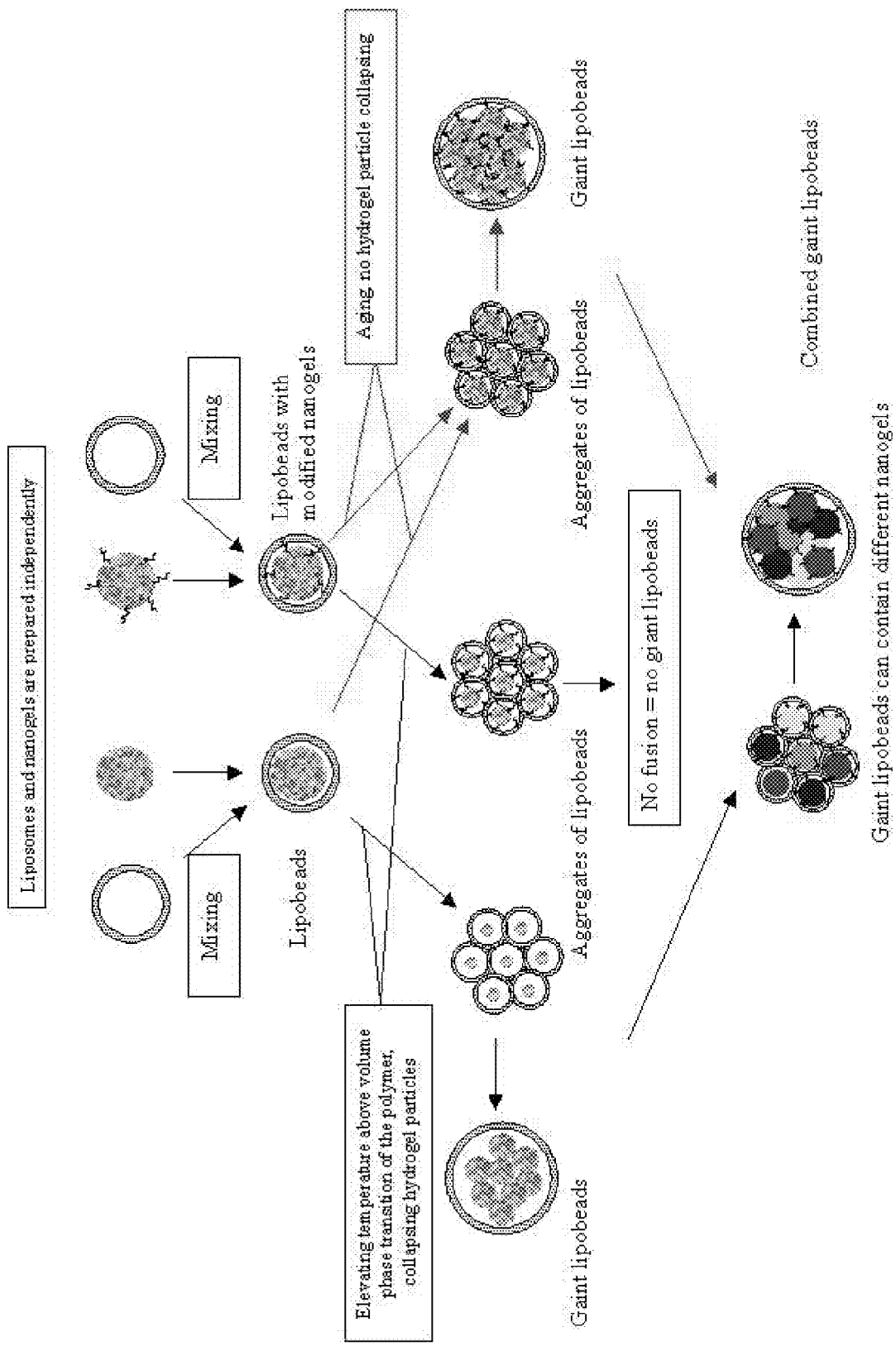
FIG. 2 is a scheme depicting lipobead preparation by constructing liposomes and nanogels independently and then mixing them together.
Figure 11:
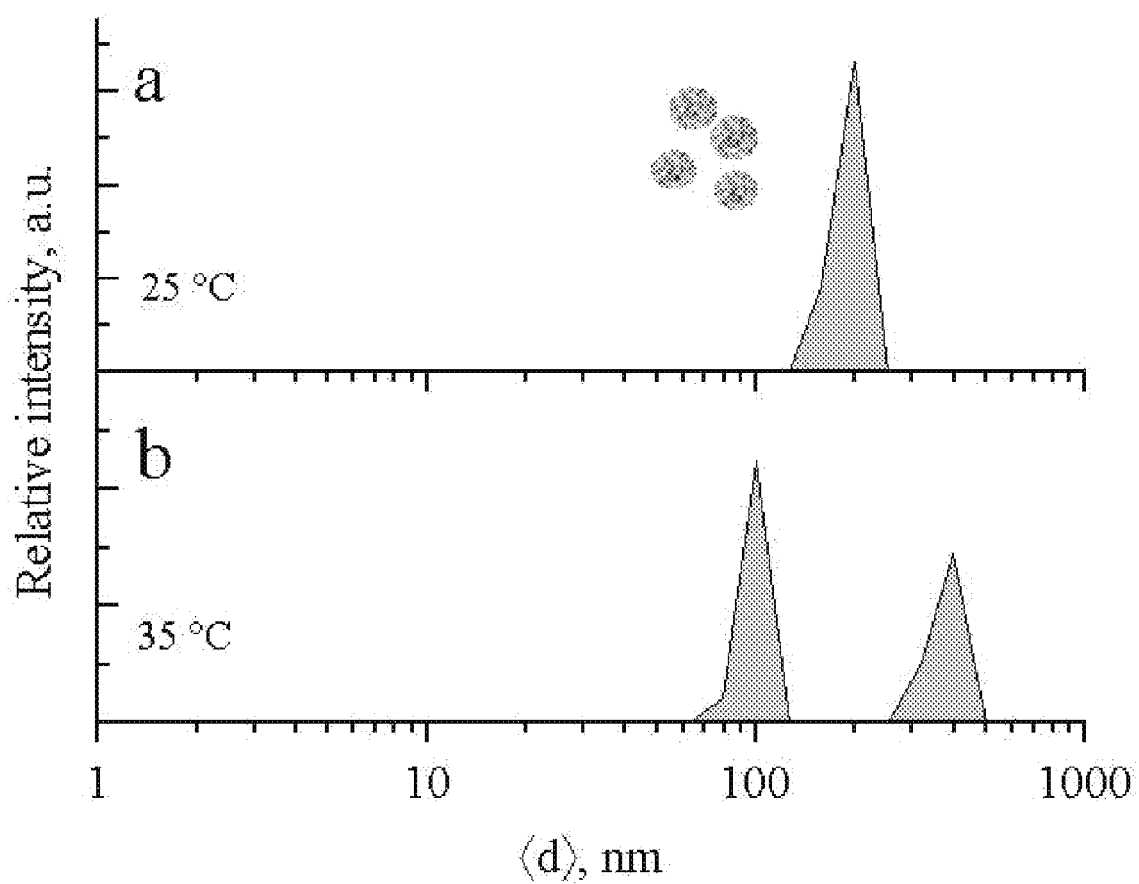
FIG. 11 shows graphs of the size distribution curves for the pure PNIPA hydrogel particles in water (a) below and (b) above the volume phase transition temperature.

The first method prepares liposomes before gelation and then polymerizes hydrogel-forming components inside the liposomes, as shown in FIG. 1. This method has the advantage of forming a more stable lipid bilayer. However, nanogels inside the liposomes are unable to undergo further modifying treatments such as loading, entrapment, or surface functionalization. Such procedures should be planned in the course of gelation instead. Lipobead fusion and formation of "giant" or combined lipobeads is impossible using this method. Polymerizing anchored or unanchored hydrogel-forming components within liposomes was described in U.S. patent application Ser. No. 10/218,554, filed concurrently with the '553 application on Aug. 14, 2002, entitled NANOGELS AND THEIR PRODUCTION USING LIPOSOMES AS REACTORS, by Sergey Kazakov, Marian Kaholek, and Kalle Levon The second method prepares liposomes and nanogels independently, as shown in FIG. 2. Using this method, penetration by a nanogel into a liposome ruptures the liposome's lipid bilayer. However, the lipid bilayer on the surface of nanogels is strong and stable enough to mask the nanogels' sensitivity to changes in external conditions. For example, the sensitivity of PNIPA-VI lipobeads to temperature and pH was masked due to their lipid bilayer coat (See FIG. 11). The advantage of fabricating liposomes and nanogels independently is that nanogels can be loaded with different compartments, filled with different liquid media, or/and functionalized with specific ligands before they are coated by a lipid bilayer. Using this method, lipobeads may fuse to form giant lipobeads.

Using the second method depicted in FIG. 2, lipobeads may be prepared by adding a liposome suspension to a solution of unanchored or anchored hydrogel particles. Incubating this solution for 1 to 4 hours at a temperature above the phase transition temperature of the phospholipid (Phospholipids' phase transition temperatures typically range from approximately −16 to +74° C. For example, egg phosphatidylcholine (EPC) has $T_p$=−2° C.) and vortexing until the suspension starts to become homogeneous (5-10 min) results in forming lipid bilayer-coated hydrogel particles.

In an exemplary embodiment of the present invention, unanchored poly(N-isopropylacrylamide) (PNIPA) hydrogel particles (formed from 5-10 wt. % hydrogel-forming components) were mixed in a 1:1 ratio with liposomes (formed from 5-10 mg/mL phospholipid in water or buffer), incubated for 2 hours at room temperature and vortexed to generate unanchored PNIPA lipobeads.

FIGS. 3a and 3b show the size distribution curves for the pure liposomes and pure PNIPA nanogels with approximately the same average diameter of approximately 180 nm. Adding liposomes to the suspension of pure PNIPA nanogels and observing the sizes of the resulting structures allows one to determine if lipobeads form or if the particles remain separated. If both particles existed independently without interactions, one could expect that upon increasing temperature the hydrogel particles would shrink, whereas liposomal sizes would not change, and two separate peaks would be detected. If both particles formed aggregates, however, the resulting particles should be at least twice their initial average size, as was seen in FIGS. 4d and 3b.

DLS measurements of the PNIPA nanogel/liposome mixture detected a single peak (FIG. 3c) with an average diameter slightly greater than diameter of the initial liposomes and the PNIPA nanogels at 25° C. (e.g., below $T_V$ for PNIPA gels). The single peak (FIG. 3d) significantly shifted towards larger diameters at 40° C. (e.g., above $T_V$ for PNIPA gels). This unexpected behavior of the hydrogel particles/liposomes mixture can be explained only by assuming that, during mixing, the liposomes' phospholipid bilayer covers PNIPA nanogels resulting in lipobeads, as illustrated in FIG. 3c. Apparently, this configuration is energetically more preferable over the others. Note that considerable hydrophobicity of the PNIPA gel might be hidden within the liposome.

In another exemplary embodiment of the present invention, anchored PNIPA-VI lipobeads were generated by mixing PNIPA-VI nanogels (formed from 5-15 wt. % hydrogel-forming components) with liposomes (formed from 5-10 mg/mL phospholipid in water or buffer) in a 1:1 ratio, incubating the mixture for 2 hours at room temperature and vortexing.

Figure 3:
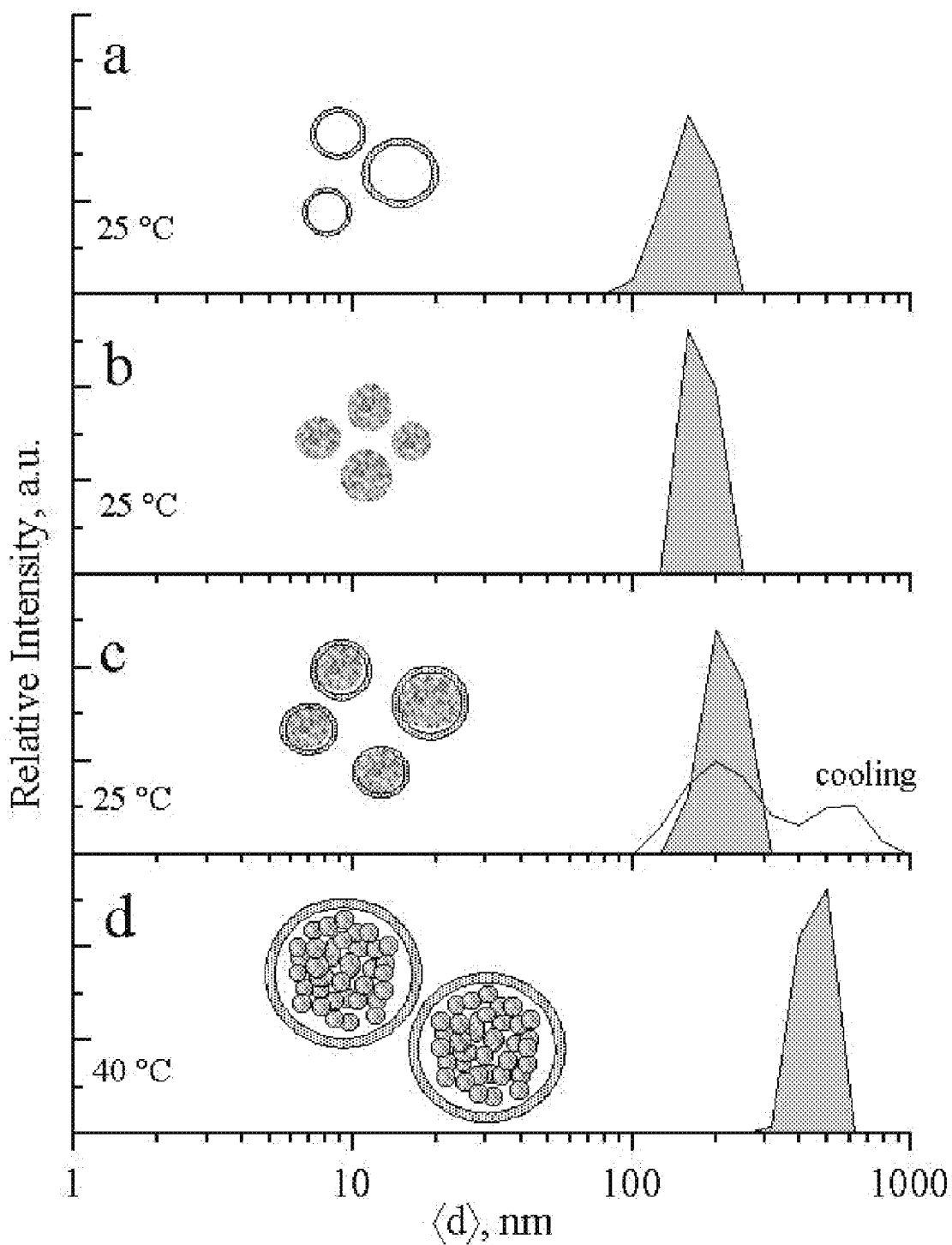
FIG. 3 shows graphs of the size distribution curves for (a) liposomes, (b) pure PNIPA nanogels, and their mixture below (c) and above (d) the volume phase transition temperature.
Figure 4:
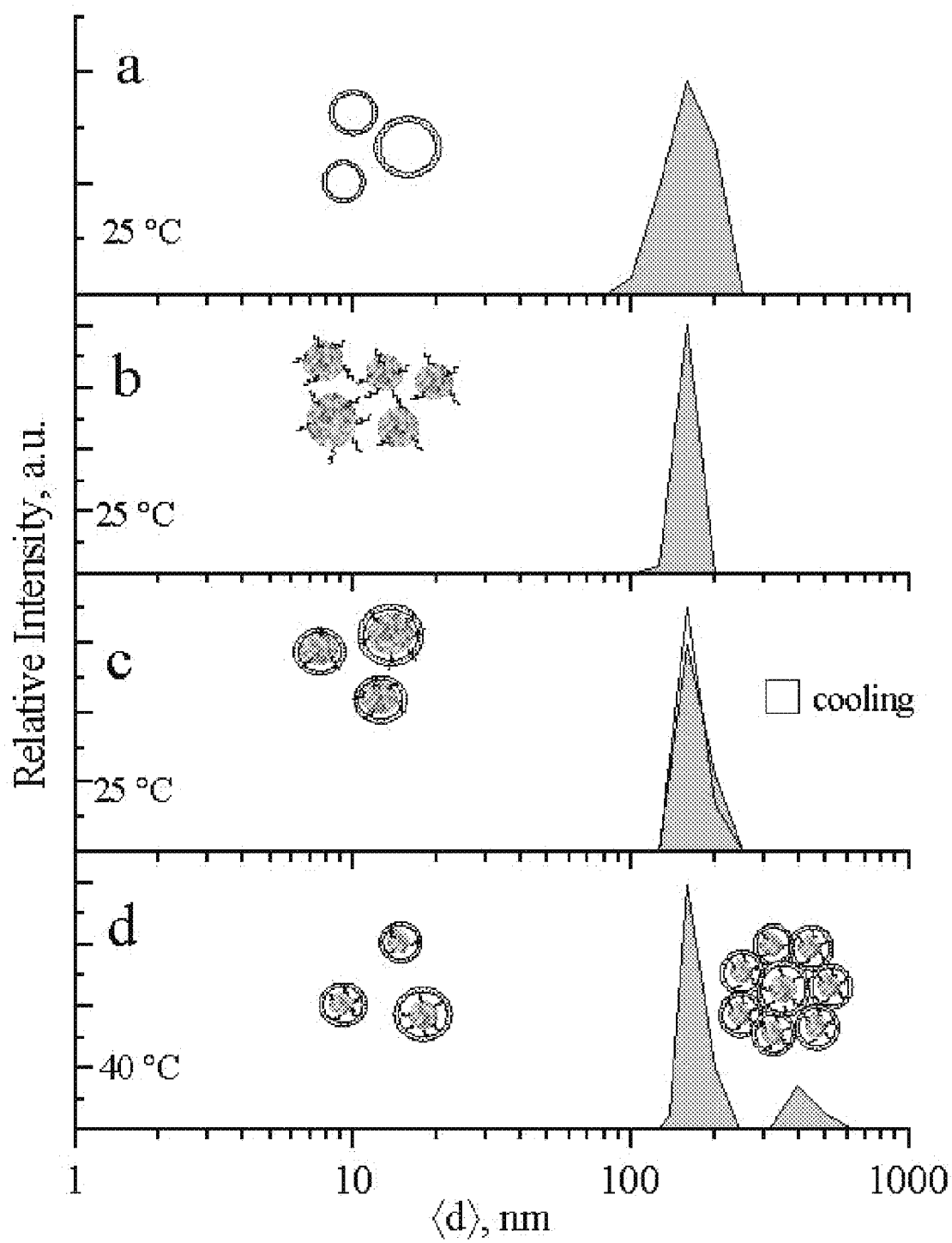
FIG. 4 shows graphs of the size distribution curves for (a) liposomes, (b) anchored PNIPA-VI nanogels, and their mixture (c) below and (d) above the volume phase transition temperature.
Figure 5:
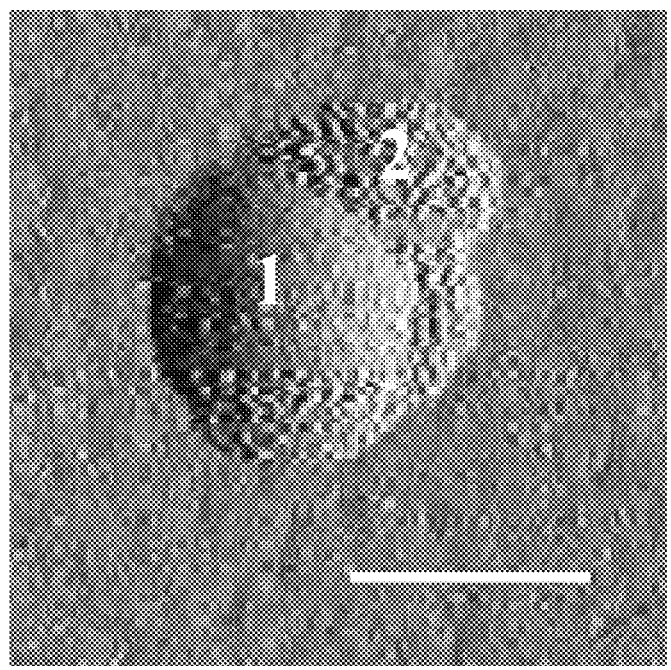
FIG. 5 is a tapping mode Atomic Force Microscopy (AFM) image (amplitude data) of the anchored PNIPA-VI nanogel (1) coated by a lipid bilayer (2) obtained after mixing PNIPA-VI nanogels with liposomes at 25° C. (bar=100 nm).

FIGS. 4a and 4b show the size distribution curves for liposomes and pure anchored PNIPA-VI nanogels with average diameters of approximately 160 nm, as was seen with PNIPA nanogels and liposomes (See FIG. 3). Mixing the liposomes and the anchored PNIPA-VI nanogels resulted in lipobeads with the size distribution curve shown in FIG. 4c. These three curves imply that the size distribution of the lipobeads is determined by the size distribution of the nanogels. Similar to mixing unanchored PNIPA nanogels and liposomes, each anchored PNIPA-VI hydrogel particle (1) is coated with a liposomes' phospholipid bilayer (2), forming a lipobead during mixing, as shown in FIG. 5.

Figure 6:
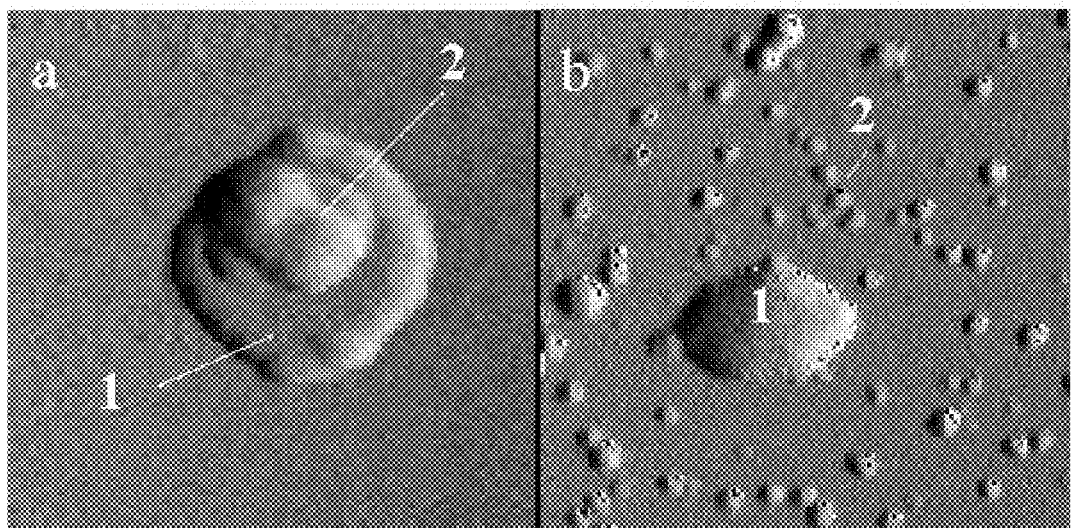
FIGS. 6a and 6b are AFM images (amplitude data) of (a) a PNIPA-VI lipobead after gelation inside liposomes (frame 400×400 nm$^2$; 1, flattened lipid bilayer; 2, nanogel); and (b) mixed phospholipid/detergent micelles and a nanogel after lipid bilayer solubilization (frame 440×440 nm$^2$; 1, nanogel; 2, mixed micelles).

Polymerizing PNIPA-VI nanogels within liposomes also, as per U.S. patent application Ser. No. 10/218,554, filed concurrently with the '553 application on Aug. 14, 2002, entitled NANOGELS AND THEIR PRODUCTION USING LIPOSOMES AS REACTORS, by Sergey Kazakov, Marian Kaholek, and Kalle Levon, generated anchored PNIPA-VI lipobeads. Introducing water-insoluble N-octadecylacrylamide (ODAm) into the liposomal membrane on the step of the dry phospholipid film formation resulted in nanogels anchored to their liposomal reactors. Hydrophobic residues penetrated into the lipid bilayer during liposome formation, and hydrophilic heads of ODAm were covalently bound to the polar end groups of the PNIPA-VI chains on the surface of the network during UV-copolymerization. As a result, anchored PNIPA-VI lipobeads (See FIG. 6a) with the diameter of around 200 nm (See FIG. 7a) were synthesized.

Figure 8:
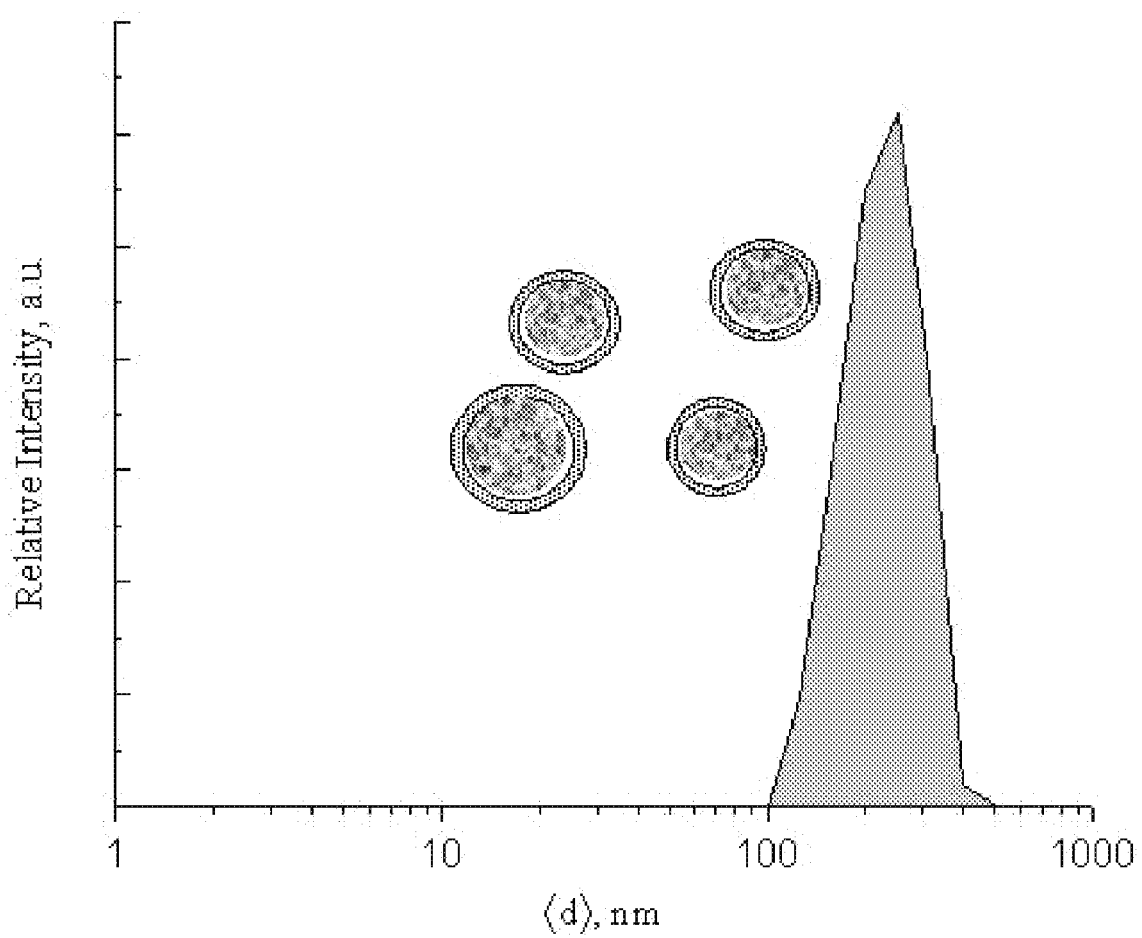
FIG. 8 shows a graph of the size distribution curve for PAAm lipobeads in buffer.

Similarly, poly(acrylamide) (PAAm) hydrogels were generated as described in U.S. patent application Ser. No. 10/218,554, filed concurrently with the '553 application on Aug. 14, 2002, entitled NANOGELS AND THEIR PRODUCTION USING LIPOSOMES AS REACTORS, by Sergey Kazakov, Marian Kaholek, and Kalle Levon. FIG. 8 shows a typical particle size distribution and structure of the lipobeads obtained after polymerization within liposomal microreactors.

Generating Giant Lipobeads

"Giant" lipobeads may be produced when lipobeads aggregate quickly due to collapsing the hydrogel particles or slowly due to long-term aging (See FIG. 2).

Combining liposomes with hydrogel particles to form lipobeads and providing the environmental conditions under which the hydrogel particles collapse and the lipobeads aggregate together produces giant lipobeads. Collapsing unanchored lipobeads and incubating for 1 to 4 hours at a temperature exceeding the volume phase transition temperature of the polymer results in the formation of lipid bilayer-coated hydrogel aggregates, or giant lipobeads.

Anchored nanogels also may shrink inside liposomes due to temperatures above $T_V$ and partially aggregate, but the hydrophobic chains (anchors) on their surface stabilize the lipid bilayer and prevent fusion, thus prohibiting giant lipobeads from forming.

However, lipobeads with anchored or unanchored nanogels may form giant lipobeads after long-term aging (2-3 months) at a temperature below the volume phase transition temperature of the polymer. (Lipobeads remain stable for approximately 1 month because the hydrogel stabilizes the lipid bilayer.) This method of producing giant lipobeads does not involve shrinking the nanogels inside the lipobeads.

In an exemplary embodiment of the present invention, unanchored hydrogel particles are mixed with liposomes. Incubating the mixture for 2 hours at a temperature above the volume phase transition temperature (32° C. for PNIPA nanogels) forms lipobeads. Heating to 40° C. causes the nanogels to collapse inside the lipobeads, reducing their total hydrophobic surface area and resulting in lipobead aggregation. After incubating the mixture for 20 minutes at elevated temperatures, the aggregated lipobeads' lipid bilayers fuse to yield giant lipobeads with a structure depicted in FIG. 3d for PNIPA lipobeads.

Figure 9:
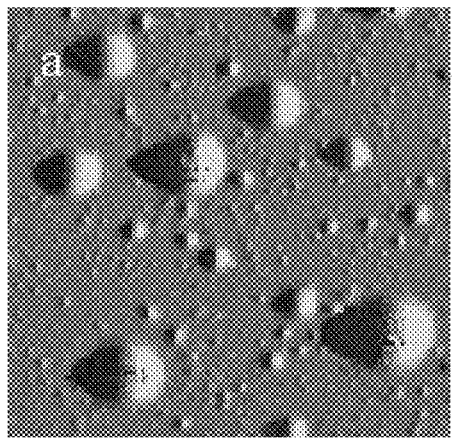
FIGS. 9a and 9b are (a) an AFM images (amplitude data) of giant lipobeads produced by long-term aging of a mixture of EPC liposomes and PNIPA-VI nanogels after three months (frame 10×10 μm$^2$) and (b) a schematic presentation of the giant lipobeads formation in aging.
Figure 9:
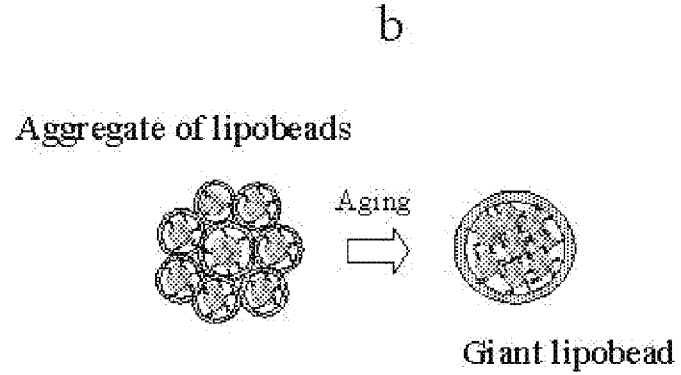

In another exemplary embodiment of the present invention, PNIPA and PNIPA-VI lipobeads aggregate and form giant lipobeads at room temperature (i.e., below volume phase transition temperature) without shrinking the nanogels inside the lipobeads. Aggregation and giant lipobeads formation occur over the course of long-term aging (2-3 months) of the lipobeads. An AFM image (amplitude data) of anchored PNIPA-VI giant lipobeads after three months storage at +4° C. is presented in FIG. 9.

Properties of Systems Generated

One goal of the present invention is to produce a system that mimics biological entities and responds quickly to changes in environmental conditions such as pH, ions, and temperature. Properties of liposomes and nanogels are described in §4.2.1 and §4.2.2, respectively. Properties of lipobeads and giant lipobeads are described in §4.2.3 and §4.2.4, respectively.

Properties of Liposomes

U.S. patent application Ser. No. 10/218,554, filed concurrently with the '553 application on Aug. 14, 2002, entitled NANOGELS AND THEIR PRODUCTION USING LIPOSOMES AS REACTORS, by Sergey Kazakov, Marian Kaholek, and Kalle Levon showed that LUV liposomes had a size distribution between 30 and 1000 nm.

Figure 10:
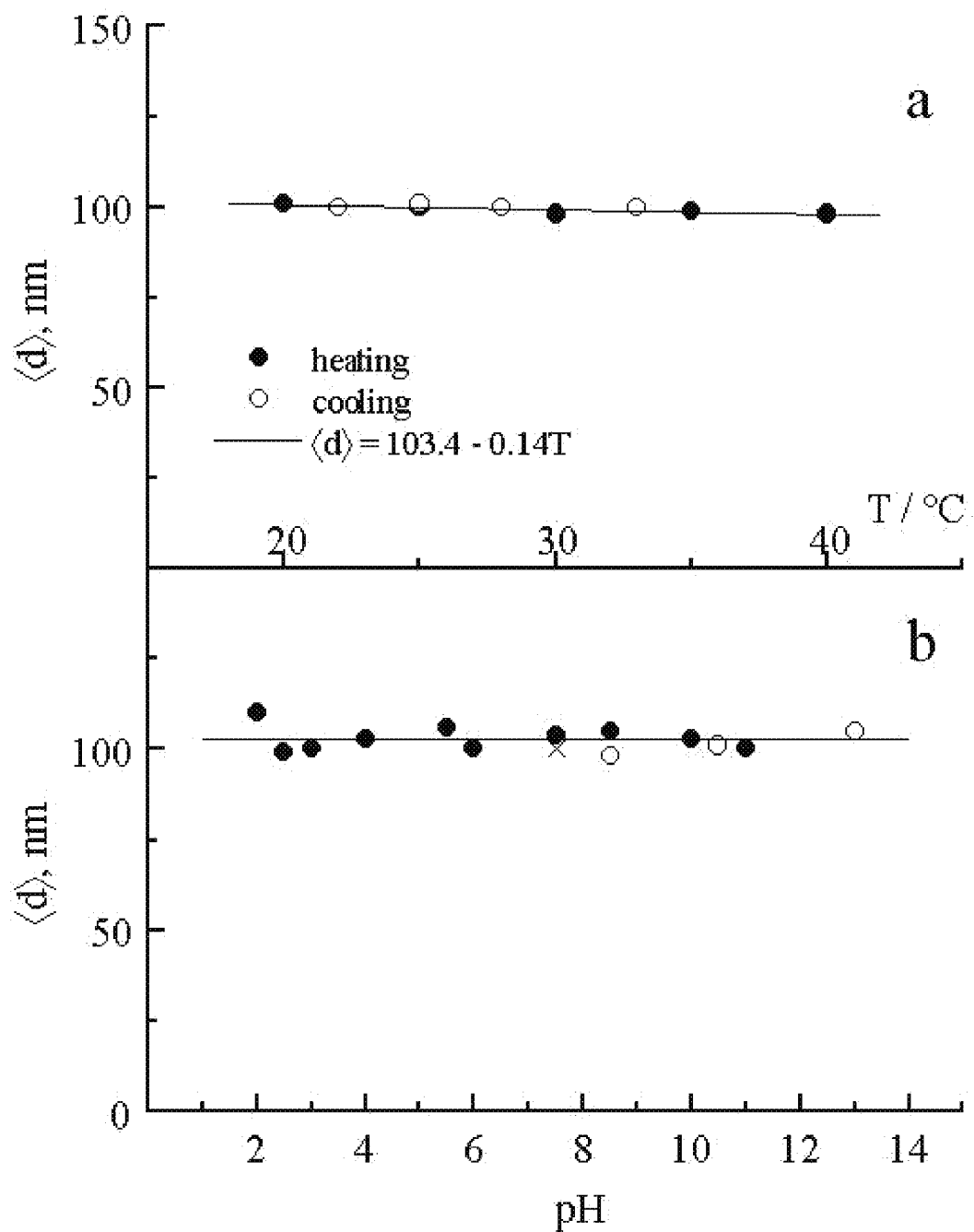
FIG. 10 shows graphs of (a) the Z-average diameter of liposomes as a function of temperature during heating/cooling cycles and (b) pH Dependence of the average diameter of the liposomes.

The temperature dependence of the apparent diameter of egg phosphatidylcholine (EPC) liposomes between 20 and 40° C. is shown in FIG. 10a. In the temperature range above the main transition temperature (–2° C.), there was a slight decrease in <d> with an increasing temperature. The decrease was less than 5% in the range studied. There was almost no difference in <d> between the heating (solid circles) and the cooling (open circles), indicating a reversible change without thermal hysteresis.

FIG. 10b shows the pH independence of the apparent diameter of EPC liposomes. As seen in FIG. 10b, liposomes were prepared at pH 7.5 (initial point, X); pH was increased by addition of 0.2 M NaOH (open circles) and decreased by addition of 0.1 M HCl (solid circles). Since EPC is a neutral phospholipid, pH-responsive fusion of its lipid bilayer is not expected. However, DLS revealed a tendency of liposomes to aggregate at low pH (pH<3), a result ascribed to possible protonation and neutralization of the $P^-$-$N^+$ dipole in phosphocholine on the liposome interface and/or to destruction of the hydration shell including interfacial water molecules in close contact with lipid polar head-groups.

Properties of Nanogels

Poly(N-isopropylacrylamide) (PNIPA) and poly(N-isopropylacrylamide-co-1-vinylimidazole) (PNIPA-VI) nanogels were characterized in terms of their response to changes in environmental conditions. In the following, properties of PNIPA and PNIPA-VI nanogels are described in §4.2.2.1 and §4.2.2.2, respectively.

Properties of PNIPA Nanogels

Figure 12:
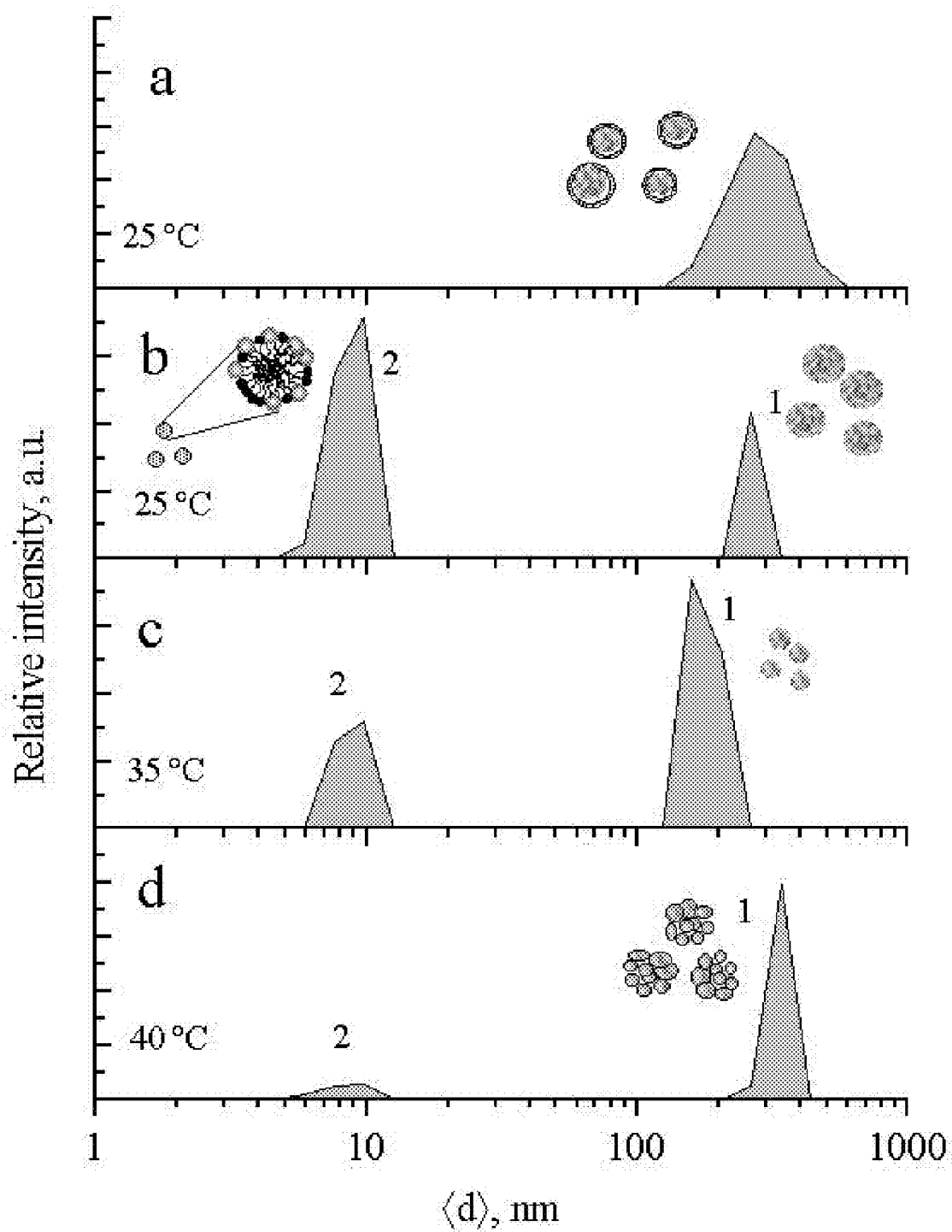
FIG. 12 shows graphs of the size distribution curves for (a) PNIPA lipobeads in buffer at 25° C., (b) after addition of 15 mM $T_{X-100}$ at 25° C., (c) at 35° C., and (d) at 40° C.

After removing solubilized phospholipid and detergent molecules and mixed micelles by dialysis against water and concentrating this suspension by evaporation in a temperature gradient, resultant PNIPA nanogels have average diameters of around 200 nm (FIG. 11a), considerably smaller than that for the nanogels in solution containing detergent and lipid molecules (cf. FIG. 12b). This finding indicates that PNIPA hydrogel particles in the surfactant solution can accommodate some surfactant molecules on the surface or/and within the gel network, e.g., in the form of micelles.

Since PNIPA gels exhibit a volume phase transition temperature at $T_V$~32° C., increasing the temperature above $T_V$ is expected to cause shrinking of the PNIPA hydrogel particles. Interestingly, at 35° C. (FIG. 12c) the peak position for the larger particles shifted towards smaller sizes whereas at 40° C. (FIG. 12d) the peak moved to larger sizes. Herein, the absolute intensities of light scattered from small particles did not change but the absolute scattering intensities of large particles progressively increased upon elevating the temperature. The latter behavior can be explained only if shrunken PNIPA hydrogel particles aggregate.

Properties of PNIPA-VI Nanogels

Figure 7:
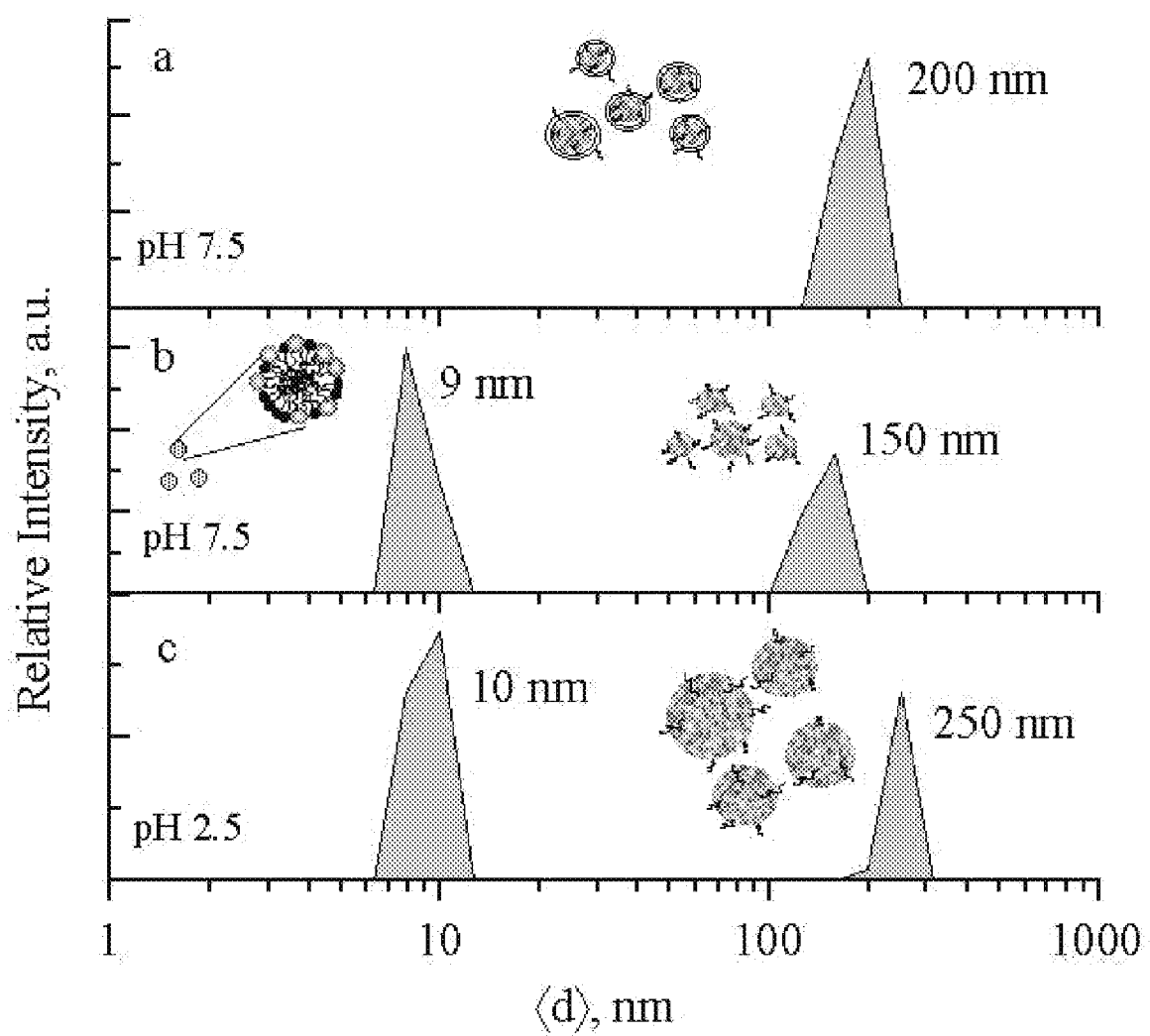
FIG. 7 shows graphs of the size distribution curves for (a) PNIPA-VI lipobeads in buffer (pH 7.5) and after addition of 15 mM $T_{X-100}$ at (b) pH 7.5 and (c) pH 2.5.

Fabricating hydrogel particles using liposomes as reactors was confirmed by removing the vesicle phospholipid bilayer from the lipobeads with detergent ($T_{X-100}$). As shown in FIG. 7b two peaks corresponding to the mixed detergent/lipid micelles (~9 nm) and the PNIPA-VI nanogels (~150 nm) appeared at pH 7.5 and 25° C. The pH was reduced to 2.5 to determine if the ionizable VI monomers were incorporated within the PNIPA network. The acidic environment should result in =NH$^+$Cl$^-$ groups in the gel particles. FIG. 7c shows that the sizes of PNIPA-VI hydrogel particles at pH 2.5 increased (~250 nm) compared with those of the gel particles with the =N— groups at pH 7.5. The estimated swelling ratio of $\alpha \approx 4.6$ demonstrates the pH-sensitivity of the prepared PNIPA-VI nanogels.

Properties of Lipobeads

Lipobeads combine the properties of liposomes and the nanogels they enclose to create a system that is sensitive to changes in environmental conditions. In the following, unanchored PNIPA lipobeads are described in §4.2.3.1 and anchored PNIPA-VI lipobeads are described in §4.2.3.2.

Properties of Unanchored PNIPA Lipobeads

PNIPA lipobeads were prepared as described in §4.1.3. FIG. 12a shows that a relatively broad size distribution of PNIPA lipobeads with a peak at around 250 nm are obtained after UV exposure of a diluted LUV suspension containing initial components of PNIPA gels (See FIG. 13, line 3). FIG. 12b demonstrates that again, addition of $T_{X-100}$ in a molar ratio of 45:1 (detergent/lipid) results in two peaks with maxima at 9 nm and 250 nm ascribed to the mixed detergent-phospholipid micelles and the PNIPA hydrogel particles, respectively. The ratio between scattering intensities of small and large particles indicates that the concentration of nanogels is relatively low.

Properties of Anchored PNIPA-VI Lipobeads

In contrast to PNIPA lipobeads, the average size of the anchored PNIPA-VI lipobeads did not change during volume phase transition (See large peak in FIG. 4d). Moreover, only a 3% increase in the total scattering intensity indicated that the aggregation of the anchored lipobeads was weak at elevated temperatures. After cooling (FIG. 4c), the size of the anchored lipobeads was entirely restored. The observed reversibility of the swelling/deswelling behavior indicates that the anchored lipobeads aggregate without fusion. In other words, they touch each other but do not form a "giant" lipobead. The aggregates of anchored lipobeads shown in FIG. 4d also disassemble more easily than the "giant" lipobeads.

Figure 14:
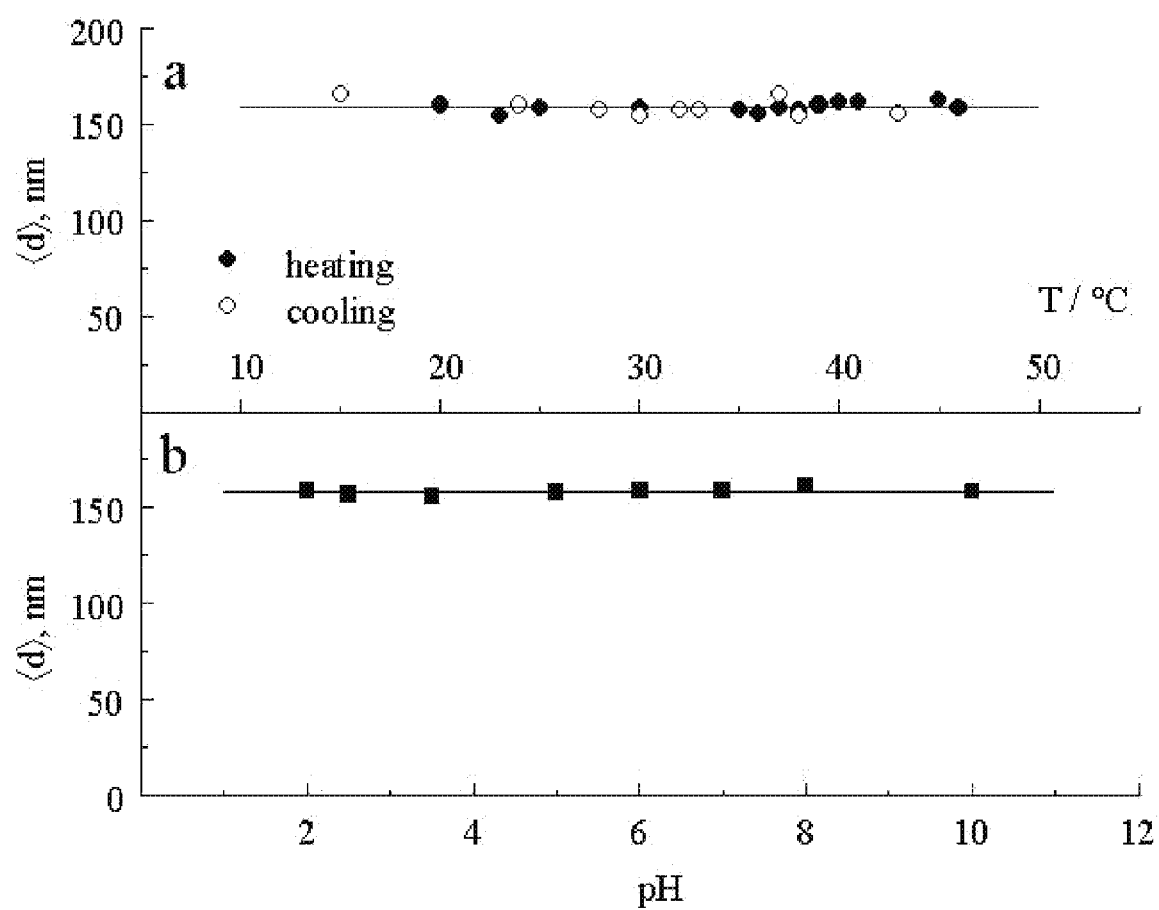
FIG. 14 is a graph of the Z-average diameter of anchored PNIPA-VI lipobeads (a) as a function of temperature upon heating/cooling cycles and (b) as a function of pH.
Figure 15:
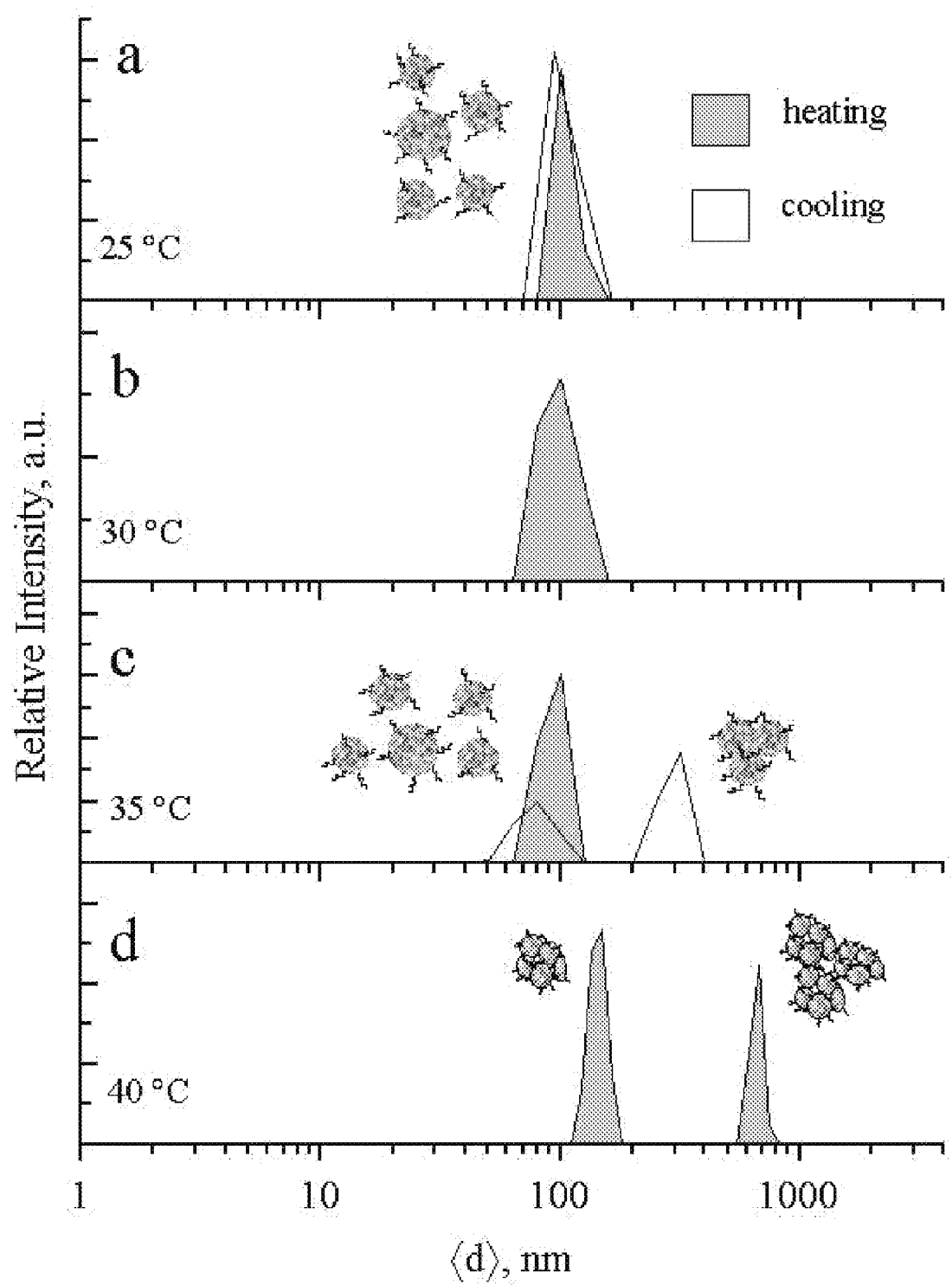
FIG. 15 includes graphs showing the effect of temperature on the collapse and subsequent aggregation of PNIPA-VI nanogels for pure PNIPA-VI nanogels in water at temperatures below, and at a temperature above, the volume phase transition temperature.
Figure 16:
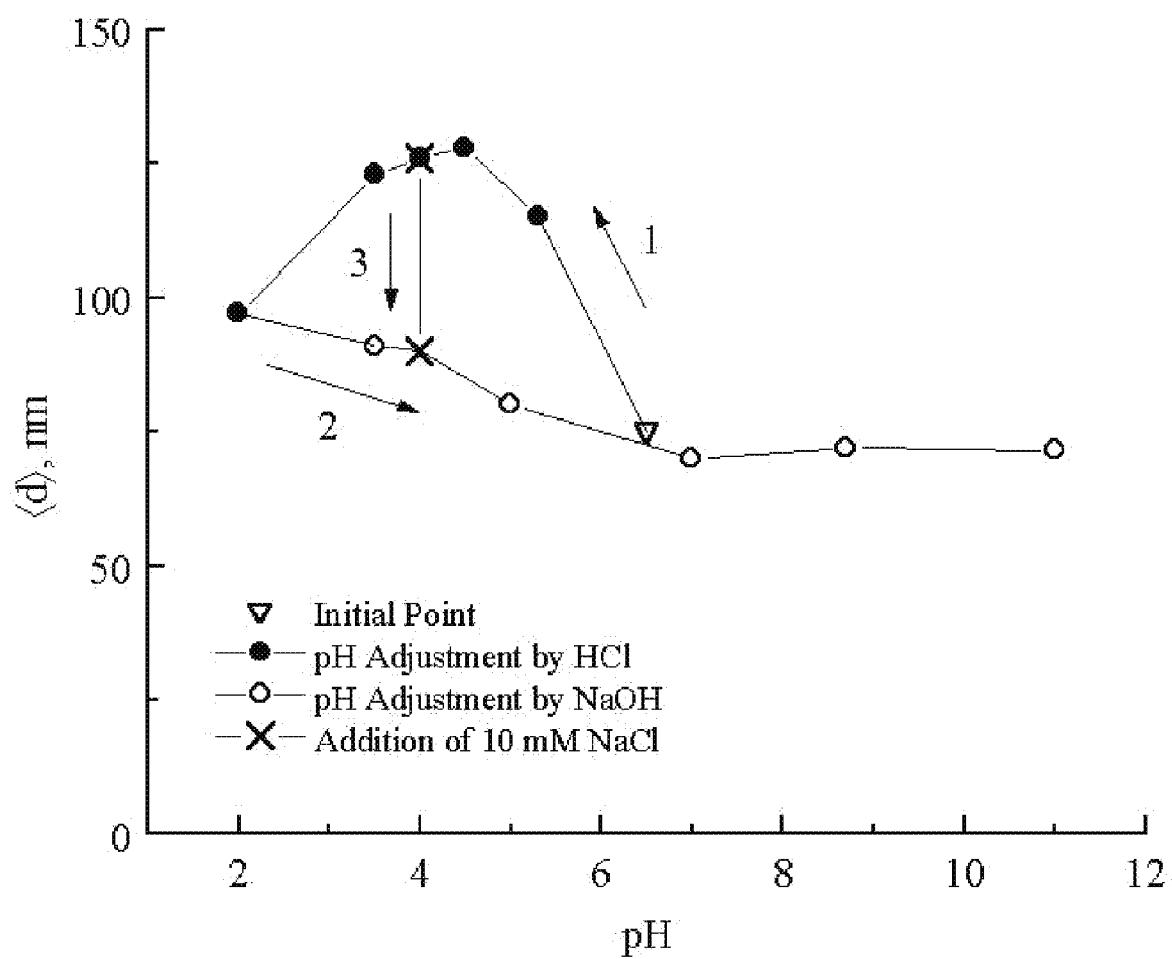
FIG. 16 is a graph showing the pH dependence of the average diameter of PNIPA-VI nanogels.

Anchored PNIPA-VI lipobeads also showed a high stability against temperature and pH changes (See FIGS. 14a and 14b, respectively). It is likely that PNIPA-VI nanogels shrink at $T_V \sim 37°$ C. (See FIG. 15) or may exhibit swelling/deswelling from pH 7 to pH 2 (See FIG. 16). However, such changes of the gel size are hidden by the temperature or pH stabilities of the lipid bilayer since the PNIPA-VI nanogels are inside the liposomes. Another reason for the pH-independence of anchored lipobeads could be that the hydrophobic chains of the anchors penetrate the bilayer, which acts as a barrier to pH changes. Thus the pH of the liposome's interior and exterior may be different.

Properties of Giant Lipobeads

Collapsing temperature-sensitive hydrogels at temperatures above $T_V$ causes fast nanogel aggregation. Data confirmed that lipobeads containing temperature-sensitive hydrogels also aggregate quickly at temperatures above $T_V$. During aggregation, fast fusion of the phospholipid bilayer also occurs if the bilayer is not stabilized by nanogels' anchors. Giant lipobead formation appeared to be irreversible. This may be due to the giant lipobeads having minimal free energy in comparison with separated and aggregated lipobeads. FIG. 3c shows the size distribution curve for PNIPA giant lipobeads after cooling to 25° C. and allowing the temperature to equilibrate for 2 hours. The resulting two peaks indicate that a portion of the giant lipobeads did not break up into elementary lipobeads.

CONCLUSIONS

As can be appreciated by the foregoing, the present invention can be used to produce lipobeads. Since such assemblies combine the properties of nanogels and liposomes, the present invention provides a system that can respond quickly to environmental changes and therefore opens up many new potential applications for lipobeads.

What is claimed is:

1. A method for producing an anchored lipobead defined by a hydrogel, having a diameter of less than 1 μm, encapsulated in a lipid bilayer, the method comprising:
   a) encapsulating hydrogel-forming components into liposomes, wherein the hydrogel-forming components include initiator, cross-linker, and polymer-forming monomers;
   b) encapsulating anchor-forming components into liposomal lipid bilayers, wherein the anchor-forming components include water-insoluble hydrophobic monomers, and
   c) co-polymerizing the polymer-forming monomers of the hydrogel-forming components and hydrophobic monomers of the anchor-forming components, thereby forming lipobeads.

2. The method of claim 1 further comprising:
   d) diluting a large unilamellar vesicles (LUV) suspension before polymerization to prevent polymerization outside the liposomes.

3. The method of claim 1 wherein the polymer-forming monomers contain a vinyl group.

4. The method of claim 1 wherein the polymer-forming monomers are selected from a group consisting of acrylamide, N-isopropylacrylamide, N-isopropylacrylamide-co-1-vinylimidazole, N,N-dimethylacrylamide, N,N-diethylacrylamide, 1-vinylimidazole, sodium acrylate, sodium methacrylate, 2-hydroxyethylmethacrylate (HEMA), N,N-dimethylaminoethyl methacrylate (DMAEMA), N-[tris(hydroxymethyl)methyl]acrylamide, 1-(3-methacryloxy)propylsulfonic acid (sodium salt), allylamine, N-acryloxysuccinimide, N-vinylcaprolactam, 1-vinyl-2-pyrrolidone, 2-acrylamido-2-methyl-1-propanesulfonic acid (sodium salt), (3-acrylamidopropyl)trimethylammonium chloride, and diallyldimethylammonium chloride.

5. The method of claim 1 wherein the liposome is selected from group consisting of egg yolk L-α-phosphatidylcholine (EPC), 1,2-dimyristoyl-sn-glycero-3-phosphatidylcholine (DMPC), 1,2-dipalmitoyl-sn-glycero-3-phosphatidylcholine (DPPC), 1,2-dioleoyl-sn-glycero-3-phosphatidylcholine (DOPC), 1,2-distearoyl-sn-glycero-3-phosphatidylcholine (DSPC), 1,2-dilauroyl-sn-glycero-3-phosphatidylcholine (DLPC), 1,2-dioleoyl-sn-glycero-3-phosphaethanolamine (DOPE), 1-palmitoyl-2-oleoyl-sn-glycero-3-phosphaethanolamine (POPE), 1,2-dimyristoyl-sn-glycero-3-phosphaethanolamine (DMPE), 1,2-dipalmitoyl-sn-glycero-3-phosphaethanolamine (DPPE), and 1,2-distearoyl-sn-glycero-3-phospharthanolamine (DSPE).

6. The method of claim 1 wherein the cross-linker is selected from a group consisting of N,N'-methylenebisacrylamide, N,N'-(1,2-dihydroxyethylene)bisacrylamide, ethylene glycol diacrylate, di(ethylene glycol) diacrylate, tri(ethylene glycol) diacrylate, tetra(ethylene glycol) diacrylate, ethylene glycol dimethacrylate, di(ethylene glycol) dimethacrylate, tri(ethylene glycol) dimethacrylate, tetra(ethylene glycol) dimethacrylate, and pentaerythritol triacrylate.

7. The method of claim 1 wherein photopolymerization is accomplished by a photoinitiator, and wherein the photoinitiator is selected from a group consisting of 2,2-diethoxyacetophenone, 2,2-dimethoxy-2-phenylacetophenone (IRGACURE 651), 1-[4-(2-hydroxyethoxy)phenyl]-2-hydroxy-2-methyl-1-propan-1-one (IRGACURE 2959), 2-hydroxy-2-methylpropiophenone, and 2-hydroxy-4'-(2-hydroxyethoxy)-2-methylpropiophenone.

8. The method of claim 1 wherein redox polymerization is accomplished by a redox initiator, and wherein the redox initiator is selected from a group consisting of ammonium persulfate, potassium persulfate, 2,2'-azobis[2-methyl-N-(2-hydroxyethyl)propionamide (VA-086), 2,2'-azobis(2-amidinopropane)dihydrochloride (V-50), 4,4'-azobis(4-cyanovaleric acid).

9. The method of claim 1 wherein the anchor-forming components are N-alkylacrylamides.

10. The method of claim 9 wherein the N-alkylacrylamides are selected from a group consisting of N-octadecylacrylamide, N-dodecylacrylamide, and N-octylacrylamide.

11. The method of claim 1 wherein the hydrogel has a diameter of approximately 30 nm to approximately 1000 nm.

12. The method of claim 1 wherein the lipobead generated has a diameter of approximately 30 nm to approximately 1000 nm.

13. A method for producing a giant lipobead defined by an aggregated plurality of hydrogel particles, each having a diameter less than 1 μm, encapsulated in a lipid bilayer, the method comprising incubating a solution of anchored or unanchored lipobeads for more at least one month, thereby aggregating lipobeads and forming giant lipobeads.

14. The method of claim 13 wherein lipobeads are incubated at temperatures below the volume phase transition temperature of the hydrogel particles.

15. The method of claim 13 wherein the hydrogel particles encapsulated within the liposomes do not shrink.

16. The method of claim 13 wherein the lipobeads have diameters of approximately 30 nm to approximately 1000 nm.

17. The method of claim 13 wherein the giant lipobead generated has a diameter of approximately 100 nm to approximately 3000 nm.

18. The method of claim 13 wherein the hydrogel particles are formed from monomers selected from a group consisting of acrylamide, N-isopropylacrylamide, N-isopropylacrylamide-co-1-vinylimidazole, N,N-dimethylacrylamide, N,N-diethylacrylamide, 1-vinylimidazole, sodium acrylate, sodium methacrylate, 2-hydroxyethylmethacrylate (HEMA), N,N-dimethylaminoethyl methacrylate (DMAEMA), N-[tris(hydroxymethyl)methyl]acrylamide, 1-(3-methacryloxy)propylsulfonic acid (sodium salt), allylamine, N-acryloxysuccinimide, N-vinylcaprolactam, 1-vinyl-2-pyrrolidone, 2-acrylamido-2-methyl-1-propanesulfonic acid (sodium salt), (3-acrylamidopropyl)trimethylammonium chloride, and diallyldimethylammonium chloride.

19. The method of claim 13 wherein the lipid bilayer is selected from group consisting of egg yolk L-α-phosphatidylcholine (EPC), 1,2-dimyristoyl-sn-glycero-3-phosphatidylcholine (DMPC), 1,2-dipalmitoyl-sn-glycero-3-phosphatidylcholine (DPPC), 1,2-dioleoyl-sn-glycero-3-phosphatidylcholine (DOPC), 1,2-distearoyl-sn-glycero-3-phosphatidylcholine (DSPC), 1,2-dilauroyl-sn-glycero-3-phosphatidylcholine (DLPC), 1,2-dioleoyl-sn-glycero-3-phosphaethanolamine (DOPE), 1-palmitoyl-2-oleoyl-sn-glycero-3-phosphaethanolamine (POPE), 1,2-dimyristoyl-sn-glycero-3-phosphaethanolamine (DMPE), 1,2-dipalmitoyl-sn-glycero-3-phosphaethanolamine (DPPE), and 1,2-distearoyl-sn-glycero-3-phospharthanolamine (DSPE).

20. The method of claim 13 wherein the giant lipobead is a combined giant lipobead.

21. The method of claim 20 wherein the combined giant lipobead contains hydrogels loaded with different compartments.

22. The method of claim 20 wherein the combined giant lipobead contains hydrogels filled with different liquid media.

23. The method of claim 20 wherein the combined giant lipobead contains hydrogels functionalized with different ligands.

24. The method of claim 20 wherein the combined giant lipobead generated has a diameter of approximately 100 nm to approximately 3000 nm.

* * * * *